(12) United States Patent
Newby et al.

(10) Patent No.: US 11,690,753 B2
(45) Date of Patent: *Jul. 4, 2023

(54) MANDIBULAR ADVANCEMENT DEVICE

(71) Applicant: Koncept Innovators LLC, Myrtle Beach, SC (US)

(72) Inventors: Sylvan Newby, Myrtle Beach, SC (US); Bryan Devereux, Myrtle Beach, SC (US)

(73) Assignee: Koncept Innovators LLC, Myrtle Beach, SC (US)

(*) Notice: Subject to any disclaimer, the term of this patent is extended or adjusted under 35 U.S.C. 154(b) by 205 days.

This patent is subject to a terminal disclaimer.

(21) Appl. No.: 17/128,479

(22) Filed: Dec. 21, 2020

(65) Prior Publication Data
US 2021/0106456 A1 Apr. 15, 2021

Related U.S. Application Data

(63) Continuation of application No. 15/880,986, filed on Jan. 26, 2018, now Pat. No. 10,905,582.
(Continued)

(51) Int. Cl.
*A61F 5/00* (2006.01)
*A61F 5/56* (2006.01)

(52) U.S. Cl.
CPC .................. *A61F 5/566* (2013.01)

(58) Field of Classification Search
CPC .... A61C 7/08; A61C 7/36; A61C 5/14; A63B 71/085; A61F 5/37; A61F 5/56; A61F 5/566
(Continued)

(56) References Cited

U.S. PATENT DOCUMENTS

5,570,704 A 11/1996 Buzzard
6,983,752 B2 1/2006 Garabadian
(Continued)

*Primary Examiner* — Adam Baker
(74) *Attorney, Agent, or Firm* — Maskell Law PLLC; Benjamin E. Maskell (57) ABSTRACT

A mandibular advancement device having a first frame and a second frame, the first frame having a first occlusal surface and a first generally U-shaped groove, the second frame having a second occlusal surface and second generally U-shaped groove, the mandibular advancement device having a first rib protruding from the first occlusal surface of the first frame, a first upstanding sidewall protruding from the first occlusal surface of the first frame, a first inner surface of the first upstanding sidewall, the first inner surface generally parallel to, offset from, and facing the first rib, a first set of teeth on the inner surface of the first upstanding wall, the first set of teeth facing the first rib and orthogonal to the first occlusal surface, a first channel of the second occlusal surface of the second frame, the first channel in relative position to interface with the first rib, an opening of the first channel, the opening of the first channel having a width that is narrower than a width of the first rib, a second upstanding sidewall protruding from the second occlusal surface of the second frame, a first outside wall of the second upstanding sidewall, the outside wall in relative position to interface with the first inner surface of the upstanding first sidewall, and a second set of teeth on the outside wall of the second upstanding sidewall, the second set of teeth orthogonal to the second occlusal surface.

19 Claims, 10 Drawing Sheets

Related U.S. Application Data (60) Provisional application No. 62/450,826, filed on Jan. 26, 2017.

(58) Field of Classification Search
USPC ................................. 128/848, 859, 861, 862
See application file for complete search history.

(56) References Cited

U.S. PATENT DOCUMENTS

| | | |
|---|---|---|
| 8,631,800 B2 | 1/2014 | Lindsay et al. |
| 8,833,374 B2 | 9/2014 | Fallon et al. |
| 2003/0217753 A1 | 11/2003 | Thornton |
| 2006/0174897 A1* | 8/2006 | Sarkisian ................ A61F 5/566 |
| | | 128/859 |
| 2008/0135056 A1 | 6/2008 | Nelissen |
| 2012/0145166 A1 | 6/2012 | Fallon |
| 2015/0366636 A1 | 12/2015 | Zampino |

* cited by examiner

MANDIBULAR ADVANCEMENT DEVICE

This application is a continuation of U.S. patent application Ser. No. 15/880,986 filed Jan. 26, 2018 which is a is a non-provisional of, and claims the benefit of priority of, U.S. Provisional Patent Application 62/450,826 filed Jan. 26, 2017, the entirety of foregoing applications are hereby incorporated by reference.

BACKGROUND OF THE INVENTION

Field of the Invention

The embodiments of the invention relate mandibular advancement devices, and more particularly, to a mandibular advancement device that is easily adjustable by a user. Although embodiments of the invention are suitable for a wide scope of applications, it is particularly suitable for self-adjustment of a mandibular advancement device while it is the user's mouth.

Discussion of the Related Art

The prior art includes all variety and manner of mandibular advancement devices. Generally, these devices are placed in the mouth and gently displace the lower jaw forward with respect to the upper jaw. This displacement can open the airway, prevent snoring, and make it easier for the wearer to breath.

One such mandibular advancement device is disclosed in U.S. Pat. No. 8,833,374 to Fallon et. al. ("Fallon"). According to Fallon, a mandibular advancement device can be formed from an upper and lower tray having interlocking teeth. The upper and lower trays can be adjusted with respect to one another by squeezing the lower tray to disengage the interlocking teeth, sliding it to a new position, and then releasing the lower tray to reengage the interlocking teeth. See, e.g. Fallon, FIG. 3 and FIG. 10.

Another such mandibular advancement device is disclosed in U.S. Pat. No. 8,631,800 to Lindsay et. al. ("Lindsay"). According to Lindsay, a mandibular advancement device can have an upper tray and a lower tray. The lower tray can have a rail and the upper tray can have two grooves. One groove is embedded deeply in the upper tray, and the other groove is closer to the surface. The rail can initially be placed in the closer groove so that the upper and lower trays can slide with respect to one another to adjust for user preference. The rail can alternatively be disposed in the deeper groove. The deeper groove can be tight and pinch the rail to prevent further movement of the trays.

There are numerous problems with the related art. For example, with the Fallon device, the act of squeezing the lower tray can be difficult for those having limited dexterity. Because the Fallon device is small, the device can easily slip from a user's hand thus frustrating attempts by a user to adjust the device. Second, the Fallon device requires interlocking slide-channels that can require specialized tooling and sliding molds in the manufacturing process. In yet another example, the Fallon device can only be adjusted outside of the mouth because the device requires squeezing by hand. Thus, to achieve a comfortable fit, a user may have to insert, remove, and adjust multiple times before achieving the desired fit.

The Lindsay device also has short comings. For example, the deep and shallow grooves of Lindsay necessitate a device having adequate thickness to accommodate the grooves. A thick device, however, can be uncomfortable for a user to wear—particularly if the user is prone to grinding their teeth. Similarly, the Lindsay device is at least partially dependent on friction in the deep groove to prevent undesired movement of the trays. Mandibular advancement devices, however, are intended to be used in the mouth where saliva can easily lubricate components thereby reducing the coefficient of friction and the efficacy of friction-fit disclosed by Lindsay.

SUMMARY OF THE INVENTION

Accordingly, embodiments of the invention are directed to a mandibular advancement device that substantially obviates one or more of the problems due to limitations and disadvantages of the related art.

An object of embodiments of the invention is to provide a mandibular advancement device that can be adjusted in the mouth.

Another object of embodiments of the invention is to provide a mandibular advancement device that is optimized for automated manufacturing by injection molding.

Still another object of embodiments of the invention is to provide a mandibular advancement device that is easily adjustable to accommodate user preference.

Yet another object of embodiments of the invention is to provide a mandibular advancement device that can be reliably secured in variable positions of advancement.

Another object of embodiments of the invention is to provide a mandibular advancement device that positively secures the top half to the bottom half to prevent unintended sliding.

Additional features and advantages of embodiments of the invention will be set forth in the description which follows, and in part will be apparent from the description, or may be learned by practice of embodiments of the invention. The objectives and other advantages of the embodiments of the invention will be realized and attained by the structure particularly pointed out in the written description and claims hereof as well as the appended drawings.

To achieve these and other advantages and in accordance with the purpose of embodiments of the invention, as embodied and broadly described, a mandibular advancement device includes a first frame, a second frame, a first rib on the first frame, the first rib extending generally from a front side of the first frame to a back side of the first frame, a first upstanding sidewall facing the first rib, a first channel on the second frame, the first channel in relative position to interface with the first rib, and an opening of the first channel, the opening of the first channel having a width that is narrower than a width of the first rib.

In another aspect, mandibular advancement device includes a first frame, a first rib, the first rib having a wider portion disposed between a top of the first rib and a bottom of the first rib, a first set of teeth on a first side of the first rib, a second rib, the second rib having a wider portion disposed between a top of the second rib and a bottom of the second rib, a second frame, a first channel, the first having a wider portion disposed between a top of the first channel and a bottom of the first channel, the first channel disposed in relative position to interface with the first rib and in relative proportions to receive a portion of the first rib therein, a second set of teeth on a first side of the first channel, the teeth disposed in relative position to engage the first set of teeth on the first side of the first rib. The first frame and the second frame are configured to be disposed in a first position and a second position wherein, in the first position, the top of the first rib is slidably disposed on the top of the first channel and wherein, in the second position, the first rib is disposed in the first channel and the first set of teeth are engaged with the second set of teeth, and wherein, upon squeezing the first frame and the second frame together, the first rib of the first rib snaps into the first channel thereby holding the first frame and the second frame together and the first set of teeth and the second set of teeth restrict sliding of the first frame with respect to the second frame.

In yet another aspect, mandibular advancement device includes a first frame, a first set of opposing teeth, a first rib disposed between the first set of opposing teeth, a second set of opposing teeth, a second rib disposed between the second set of opposing teeth, a second frame, a third set of teeth disposed in relative position to interface with the first set of teeth, a first channel disposed between the third set of teeth, the first channel dimensioned in relative proportions and disposed in relative position to receive the first rib, a fourth set of teeth disposed in relative position to interface with the second set of teeth, and a second channel disposed between the fourth set of teeth, the second channel dimensioned in relative proportions and disposed in relative position to receive the second rib.

It is to be understood that both the foregoing general description and the following detailed description are exemplary and explanatory and are intended to provide further explanation of embodiments of the invention as claimed.

BRIEF DESCRIPTION OF THE DRAWINGS

The accompanying drawings, which are included to provide a further understanding of embodiments of the invention and are incorporated in and constitute a part of this specification, illustrate embodiments of the invention and together with the description serve to explain the principles of embodiments of the invention.

DETAILED DESCRIPTION OF THE PREFERRED EMBODIMENTS

Reference will now be made in detail to the preferred embodiments of the invention, examples of which are illustrated in the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals in the drawings denote like elements.

Figure 1:
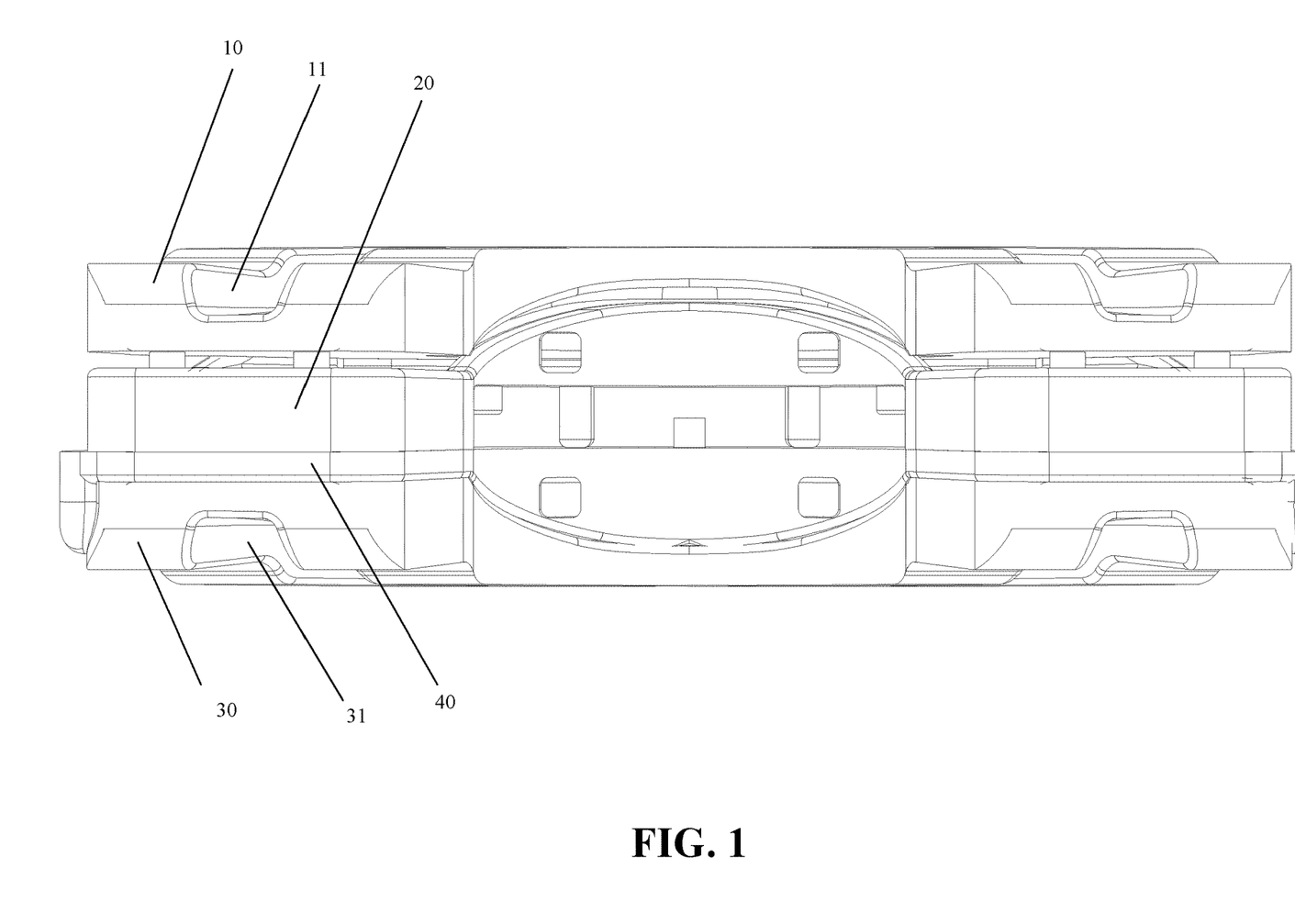
FIG. 1 is rear-side view of a mandibular advancement device according to an exemplary embodiment of the invention.

FIG. 1 is rear-side view of a mandibular advancement device according to an exemplary embodiment of the invention. As shown in FIG. 1, a mandibular advancement device can include an upper bite tray 10, an upper frame 20, a lower bite tray 30, and a lower frame 40. The upper bite tray 10 can have a groove 11 and the lower bite tray 30 have a groove 31, each groove 11 and 31 sized in approximate proportions to receive human teeth.

The upper bite tray 10 and the lower bite tray 30 can be formed from a resilient material such as silicone, rubber, plastic, latex, or a composite material. In preferred embodiments of the invention the upper bite tray 10 and the lower bite tray 30 are formed from a heat-moldable material such is commonly used in athletic mouth guards. Such heat-moldable materials can be submerged in boiling water for a few seconds, and then inserted into a user's mouth. A user can bite the heat-moldable material to conform the material to the user's unique bite. A user can further press the heat moldable material against the sides of the user's teeth and gums to achieve a snug and custom fit. Upon cooling, the heat-moldable material will set and holding the shape of the user's teeth. The upper frame 20 and the lower frame 40 can be formed from a second resilient material such as hard plastic or PVC.

Figure 2:
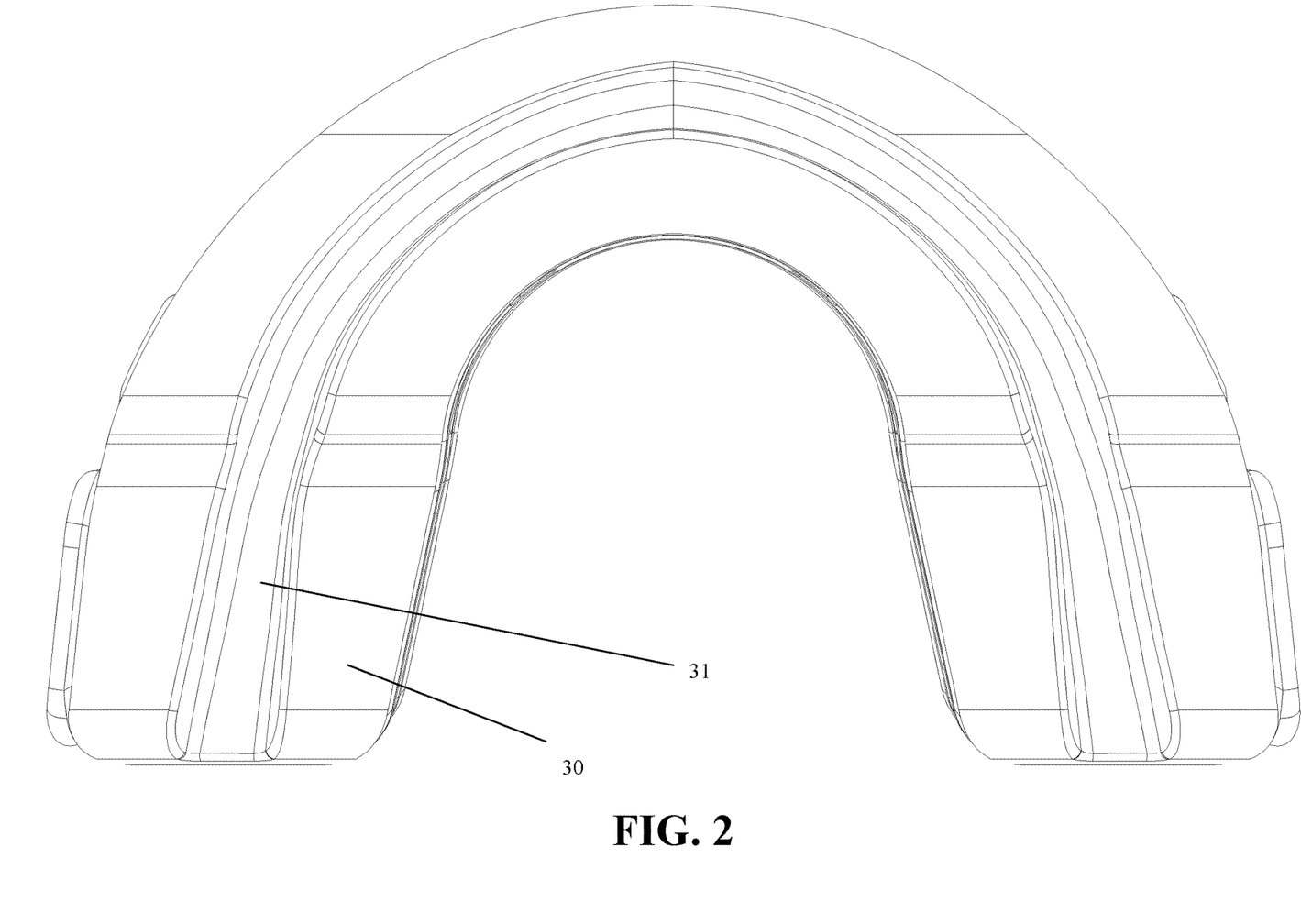
FIG. 2 is a bottom view of a mandibular advancement device according to an exemplary embodiment of the invention.

FIG. 2 is a bottom view of a mandibular advancement device according to an exemplary embodiment of the invention. As shown in FIG. 2, a mandibular advancement device can have a lower bite tray 30 on a bottom side. The lower bite tray 30 can include a U-shaped groove 31 sized in approximate proportions to receive the teeth of an adult human lower jaw.

Figure 3:
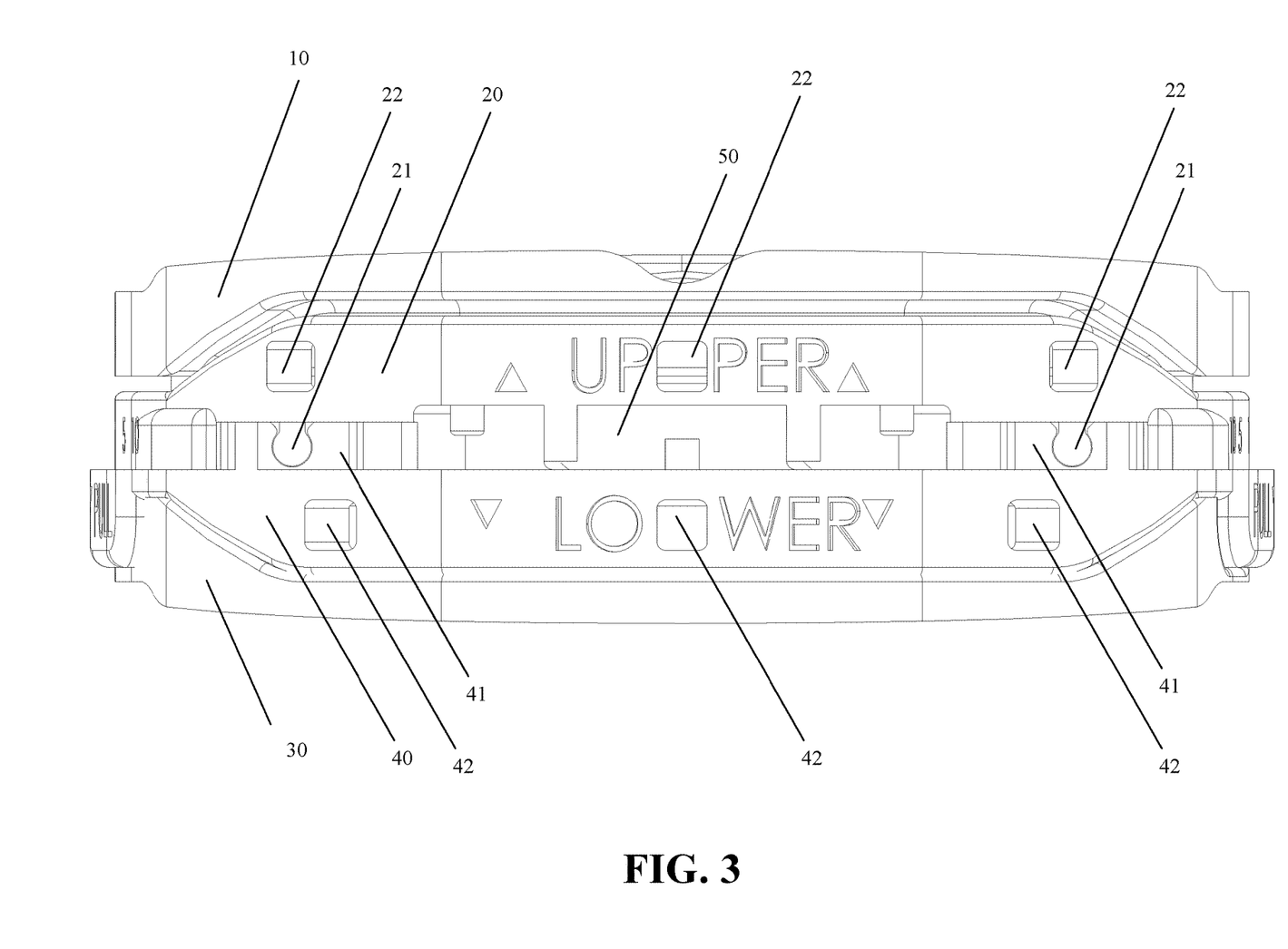
FIG. 3 is a front view of a mandibular advancement device according to an exemplary embodiment of the invention.

FIG. 3 is a front view of a mandibular advancement device according to an exemplary embodiment of the invention. As shown in FIG. 3 a mandibular advancement device can include an upper bite tray 10, and upper frame 20, a lower bite tray 30, and a lower frame 40. The upper frame 20 can have cutouts 22 to hold and receive similarly shaped protrusions of the upper bite tray 10 and can cooperate to couple the upper bite tray 10 to the upper frame 20. The lower frame 40 can have cutouts 42 to hold and receive similarly shaped protrusions of the lower bite tray 30 and can cooperate to couple the lower bite tray 30 to the lower frame 40. A space 50 between the upper frame 20 and the lower frame 40 can additionally allow air to pass. The upper frame 20 can include ribs 21 on each side. The lower frame 40 can including a mating channels 41 to receive the ribs 21. In use, the upper frame 20 can "snap" to the lower frame 40 by pressing the two halves together such that the ribs 21 are forced into the corresponding channels 41 thereby holding the two halves together.

The ribs 21 are illustrated in the attached drawings as an elongated cylinder on a pillar although it should be appreciated that other shapes and configurations would achieve the above described functionality and thus the invention is not limited to the specific shapes and configurations shown in the attached drawings.

Figure 4:
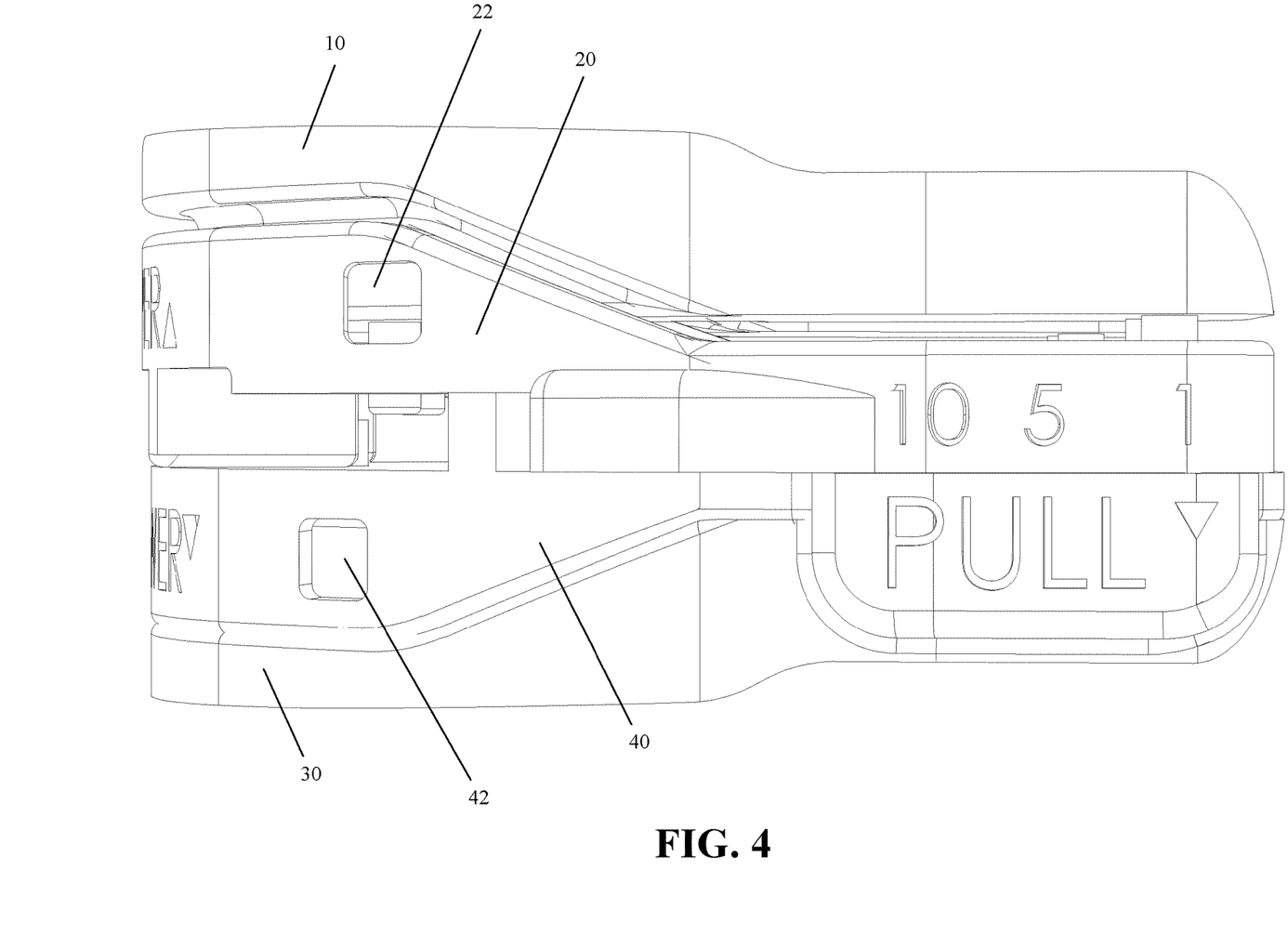
FIG. 4 is a right-side view of a mandibular advancement device according to an exemplary embodiment of the invention.

FIG. 4 is a right-side view of a mandibular advancement device according to an exemplary embodiment of the invention. As shown in FIG. 4, a mandibular advancement device can include an upper bite tray 10, and upper frame 20, a lower bite tray 30, and a lower frame 40. The upper frame 20 can have cutouts 22 to hold and receive similarly shaped protrusions of the upper bite tray 10 and can cooperate to couple the upper bite tray 10 to the upper frame 20. The lower frame 40 can have cutouts 42 to hold and receive similarly shaped protrusions of the lower bite tray 30 and can cooperate to couple the lower bite tray 30 to the lower frame 40. The cutouts 22 and 42 can receive projections (not shown) formed on the respective upper/lower bite tray 10/30 to assist in holding the assembly together.

Figure 5:
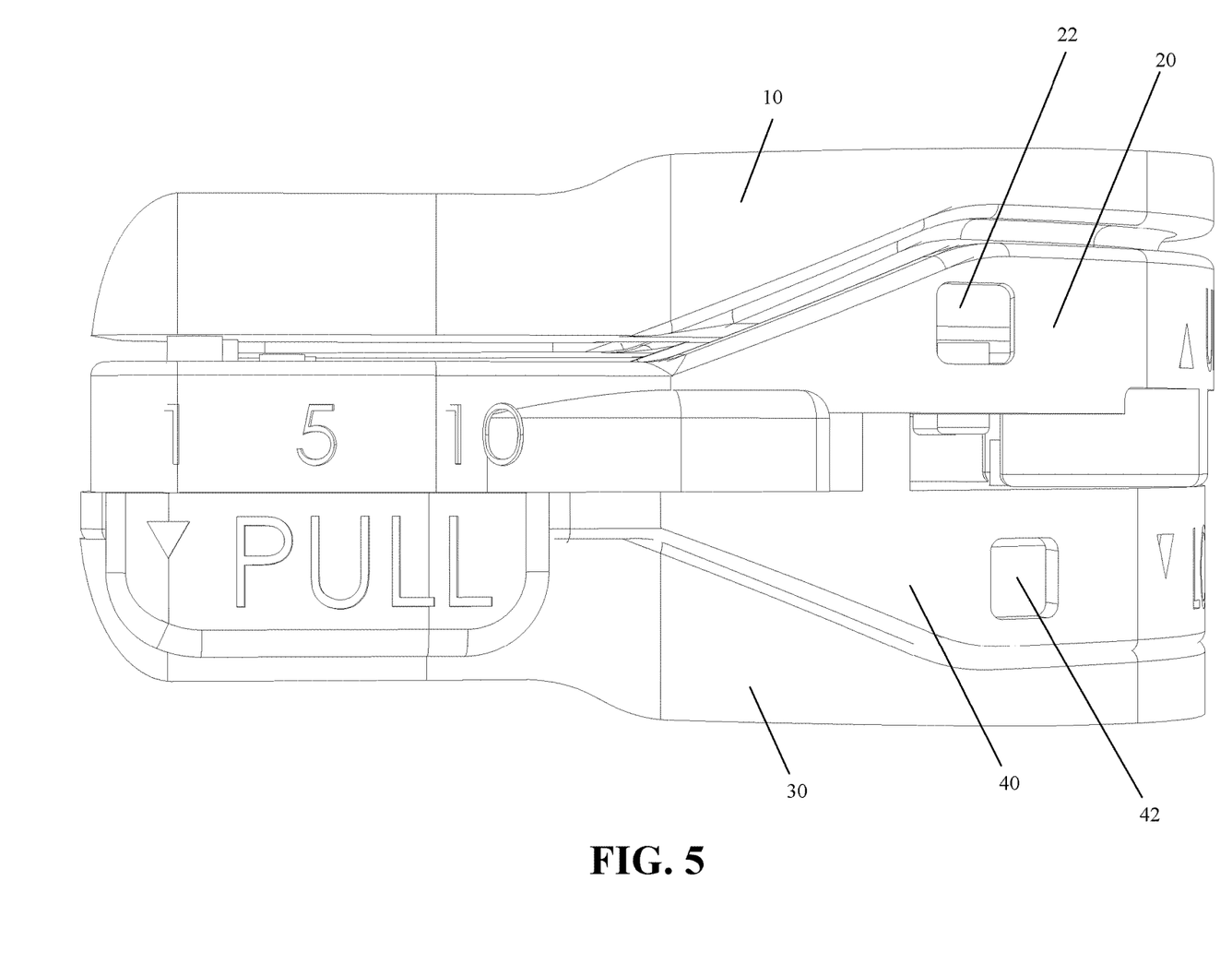
FIG. 5 is a left-side view of a mandibular advancement device according to an exemplary embodiment of the invention.

FIG. 5 is a left-side view of a mandibular advancement device according to an exemplary embodiment of the invention. As shown in FIG. 5, a mandibular advancement device can include an upper bite tray 10, and upper frame 20, a lower bite tray 30, and a lower frame 40. The upper frame 20 can have cutouts 22. The lower frame 40 can have cutouts 42.

Figure 6:
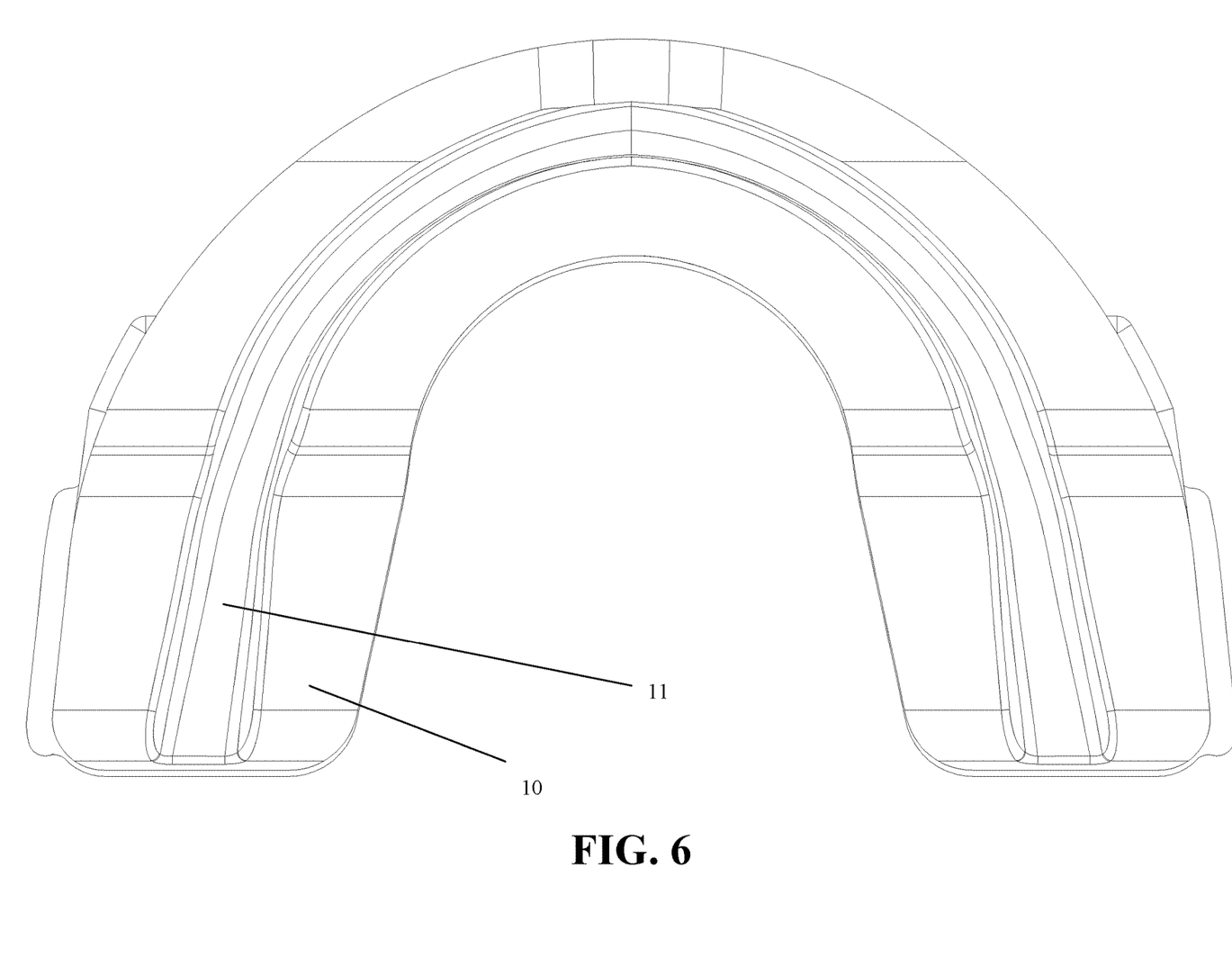
FIG. 6 is a top view of a mandibular advancement device according to an exemplary embodiment of the invention.

FIG. 6 is a top view of a mandibular advancement device according to an exemplary embodiment of the invention. As shown in FIG. 6, a mandibular advancement device can include an upper bite tray 10 and a groove 11. The groove 11 can be sized in approximate proportions to receive human teeth.

Figure 7:
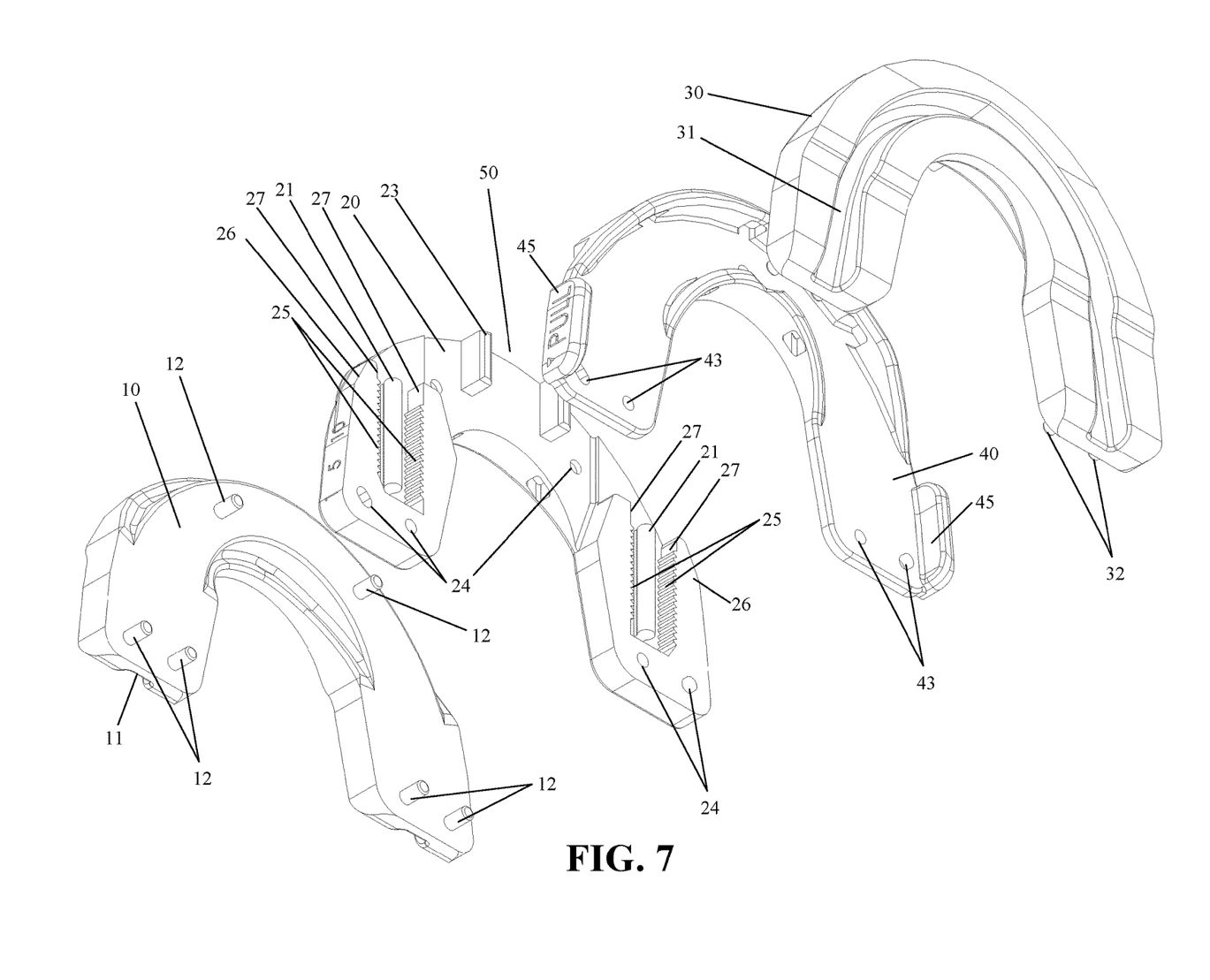
FIG. 7 is an isometric exploded view of a mandibular advancement device according to an exemplary embodiment of the invention.

FIG. 7 is an isometric exploded view of a mandibular advancement device according to an exemplary embodiment of the invention. As shown in FIG. 7, a mandibular advancement device can include an upper bite tray 10, and upper frame 20, a lower bite tray 30, and a lower frame 40. The upper bite tray 10 can have a groove 11 (partially shown) and the lower bite tray 30 have a groove 31, each groove 11 and 31 sized in approximate proportions to receive human teeth.

The upper bite tray 10 can have a plurality of projections 12. The projections 12 can mate with corresponding holes 24 in the upper frame 10. Heat can be applied to melt or weld the two pieces 10 and 20 together.

The upper frame 20 can further include ribs 21 disposed in a channel between parallel walls 27 having teeth 25 facing the rib 21. The ribs 21 can be substantially cylindrical. The ribs 21 can have opposing walls 27 that are parallel to the ribs 21. Although the embodiment of FIG. 7 is depicted as having a ribs 21 between two parallel walls 27, each having teeth 25, other configurations are contemplated and within the scope of this invention. In other embodiments, a rib may have only a single wall on one side of and parallel to the rib and only a single set of teeth on that wall. Although both sides of the upper frame 20 shown in FIG. 7 are depicted as having ribs 21 and rows of teeth 25, it is also contemplated that only one side may have a rib and that only the opposite side may have teeth.

In use, the rib 21 can be pressed into a mating portion (not shown) of the lower frame 30 to hold the upper frame 20 and the lower frame 40 together. The teeth 25 can prevent the two frames 20 and 40 from sliding fore and aft after the two halves have been pressed together. The upper frame can also include a spacer 23 in the air gap 50. The spacer can prevent the two halves from tipping and becoming disconnected when a user bites into the mandibular advancement device. The upper and lower frames 20 and 40 can be adjusted with respect to one another by placing the two frames next to each other, but not snapping them together. In this configuration, the two halves can slide fore and aft along the rib 21. When the two halves are desirably positioned, the two halves can be pressed together. When pressed together, the ribs 21 can be pressed or "snapped" into a mating channel (not shown) on the lower frame 40. When pressed together, the rib can be retained in the channel thereby locking the two halves together. Additionally, the teeth 25 can engage mating teeth on the lower frame 40 preventing the two halves from sliding with respect to one another.

In preferred embodiments of the invention, the adjustment can be performed by a user while the device is in the user's mouth. In such a use case, the two halves are placed adjacent one another such that the rib 21 is placed against the mating portion (not shown) of the lower frame 40. The assembly can then be placed in the user's mouth. While in the user's mouth, the user can move the jaw fore and aft to achieve a desirable placement. Then the user can bite thereby forcing the rib portions 21 into the corresponding mating channels (not shown) and also causing the teeth 25 to interlock with corresponding teeth (not shown) on the lower frame 40. The two halves are then locked together by way of the rib 21 and mating portion (not shown) and prevented from sliding movement by the teeth 25 and corresponding teeth (not shown) of the lower frame 40.

The upper frame 20 can further have a tab 26 that projects from a side of the frame 20. A corresponding tab 45 of the lower frame 40 can be positioned slightly offset from the tab 26 (see side views FIG. 4 and FIG. 5). The tabs 26 and 45 can assist a user to separate the two halves with by grasping the tabs between thumb and forefinger and imparting a slight twisting motion.

The lower bite tray 30 can include channels 31 for receiving the teeth of a lower jaw of a user. The lower bite tray 30 can further include projections 32. The projections 32 can be received in mating holes 43 of the lower frame. The lower frame 40 and the lower bite tray 30 can be joined by melting or welding the projections 32 into the holes 43.

Figure 8:
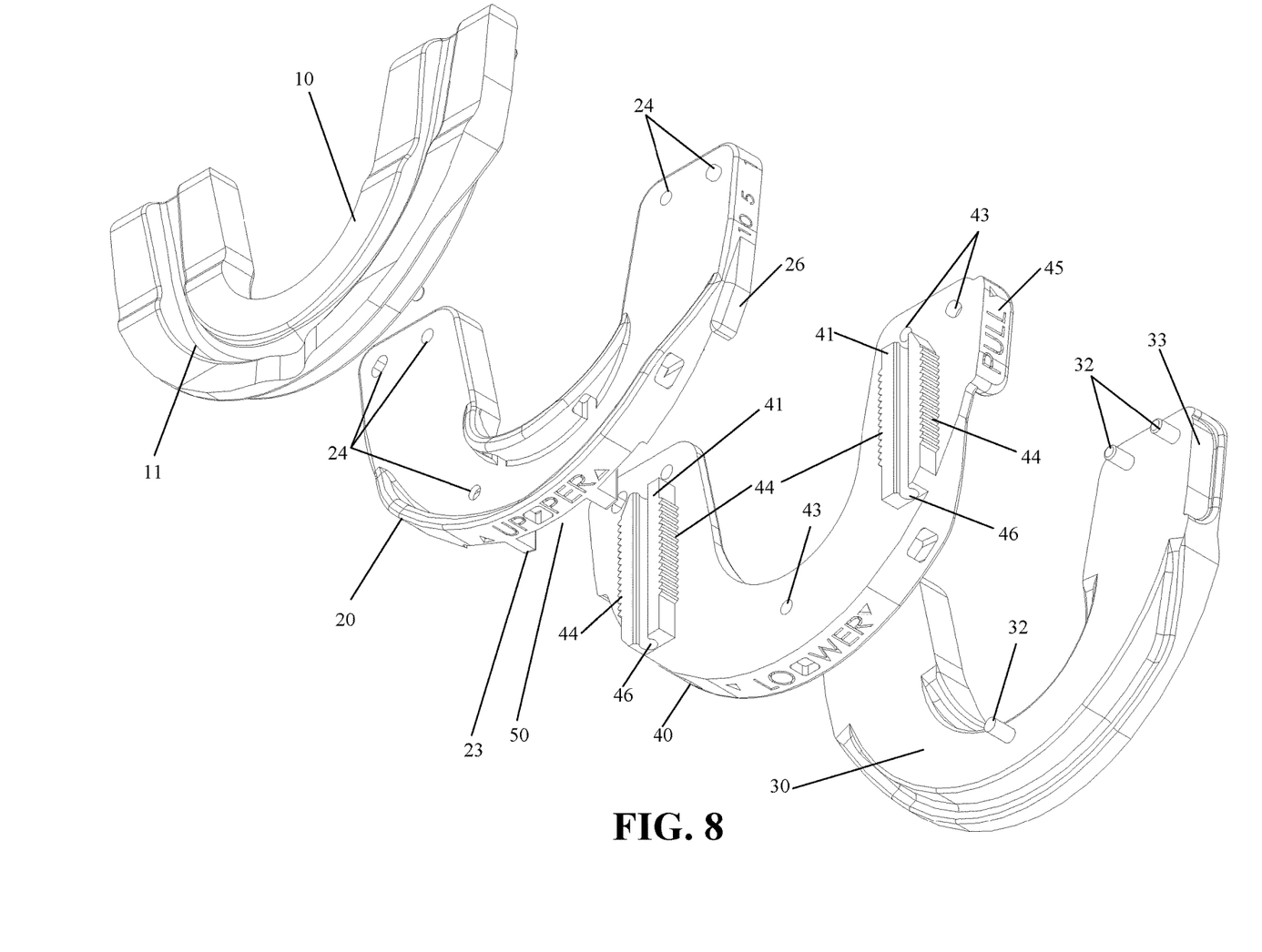
FIG. 8 is an isometric exploded view of a mandibular advancement device according to an exemplary embodiment of the invention.

FIG. 8 is an isometric exploded view of a mandibular advancement device according to an exemplary embodiment of the invention. As shown in FIG. 8, a mandibular advancement device can include an upper bite tray 10, and upper frame 20, a lower bite tray 30, and a lower frame 40. The upper bite tray 10 can have a groove 11 sized in approximate proportions to receive human teeth.

The upper bite tray 10 can have a plurality of projections (not labeled). The projections can mate with corresponding holes 24 in the upper frame 10. Heat can be applied to melt or weld the two pieces 10 and 20 together.

The upper frame 20 can further include ribs (not shown). In use, the ribs can be pressed into channels 46 of a mating portion 41 of the lower frame 30 to hold the two halves together. Teeth 44 can be disposed on an outside of mating portion 41 and parallel to the channels 46. The teeth 44 can mate with teeth (not shown) on the upper frame 20 and can prevent the two frames from sliding fore and aft after the upper frame 20 and the lower frame 40 have been pressed together. The upper frame can also include a spacer 23 in the air gap 50. The spacer 23 can prevent the two halves from tipping and becoming disconnected when a user bites into the mandibular advancement device. The upper and lower frames 20 and 40 can be adjusted with respect to one another by sliding the two halves fore and aft along the channels 46. When the two halves are desirably positioned, the two halves can be pressed together, thereby engaging the teeth 44 and locking the two halves together. In preferred embodiments of the invention, the adjustment can be performed by a user while the device is in the user's mouth. In such a use case, the two halves are placed adjacent one another such that the rib (not shown) is placed against the channels 46 of the mating portion 41 of the lower frame 40. The assembly can then be placed in the user's mouth. While in the user's mouth, the user can move the jaw fore and aft to achieve a desirable placement. Then the user can bite thereby forcing the rib (not shown) into the channels 46 of the mating portion 41 and also causing the teeth 44 to interlock with corresponding teeth (not shown) on the upper frame 20. The two halves are then locked together by way of the rib (not shown) and mating portion 41 and prevented from sliding movement by the teeth 44 and corresponding teeth (not shown) of the upper frame 20.

The upper frame 20 can further have a tab 26 that projects from a side of the frame 20. A corresponding tab 45 of the lower frame 40 can be positioned slightly offset from the tab 26 (see side views FIG. 4 and FIG. 5). The tabs 26 and 45 can assist a user to separate the two halves with by grasping the tabs between thumb and forefinger and imparting a slight twisting motion.

The lower bite tray 30 can include a groove (not shown) for receiving the teeth of a lower jaw of a user. The lower bite tray 30 can further include projections 32. The projections 32 can be received in mating holes 43 of the lower frame. The lower frame 40 and the lower bite tray 30 can be joined by melting or welding the projections 32 into the holes 43.

Figure 9:
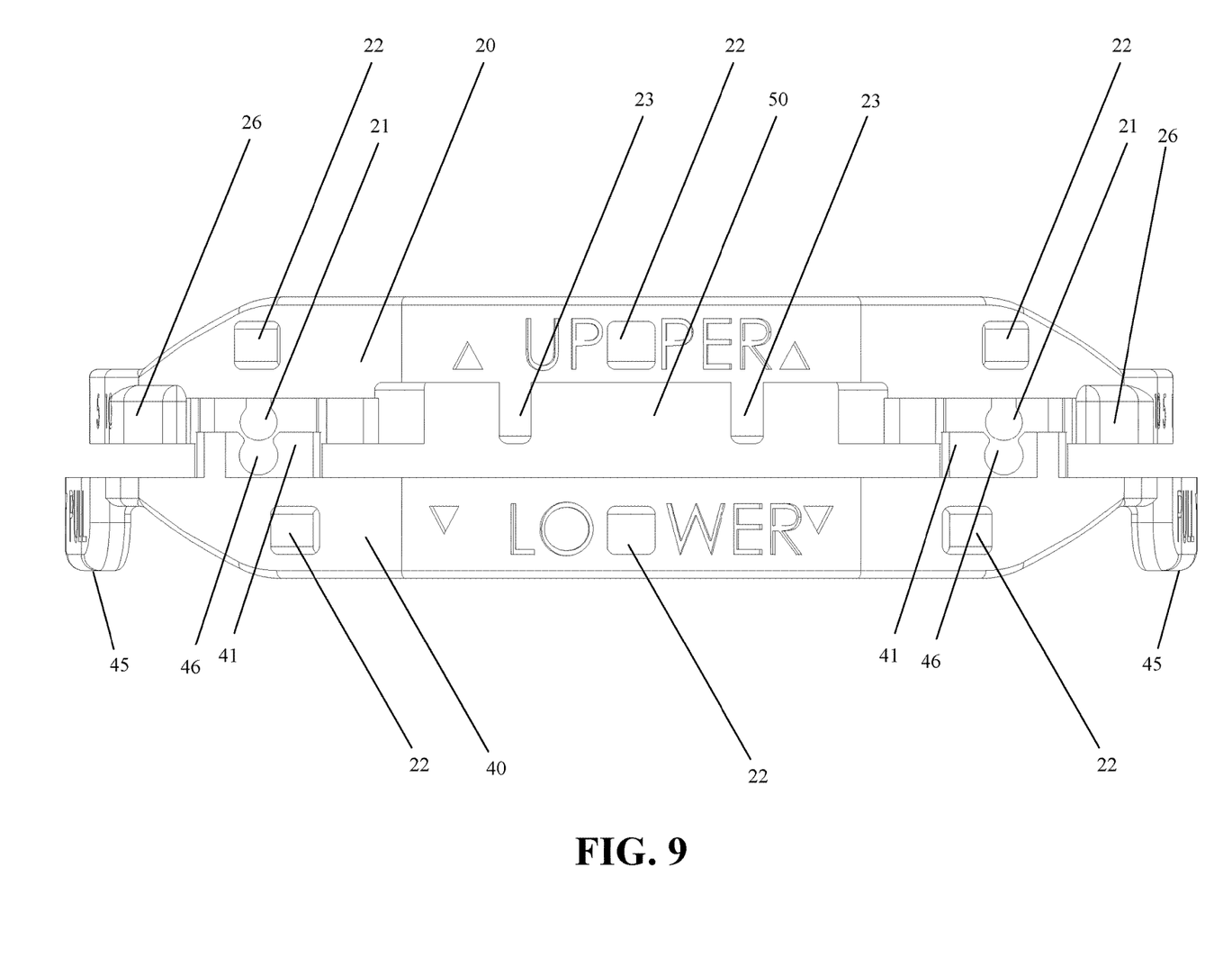
FIG. 9 is an exploded front view of a mandibular advancement device according to an exemplary embodiment of the invention.

FIG. 9 is an exploded front view of a mandibular advancement device according to an exemplary embodiment of the invention. The embodiment of FIG. 9 omits the upper and lower bite trays for clarity. As shown in FIG. 9, a mandibular advancement device can include an upper frame 20 and a lower frame 40. In the embodiment of FIG. 9, the frames 20 and 40 are shown separated. In this embodiment, the two halves are not attached to one another and can be freely separated and positioned. In this configuration, the two halves can slide fore and aft with respect to one another along the ribs 21 sliding along a top portion of the channels 46 of the mating portion 41. The two halves can be inserted in a user's mouth and desirably positioned by a user's lower jaw. When the desired position is achieved, the two halves can be pressed together by biting thereby forcing the ribs 21 into the channels 46 of the mating portions 41 and fixing the two halves in their relative positions.

Figure 10:
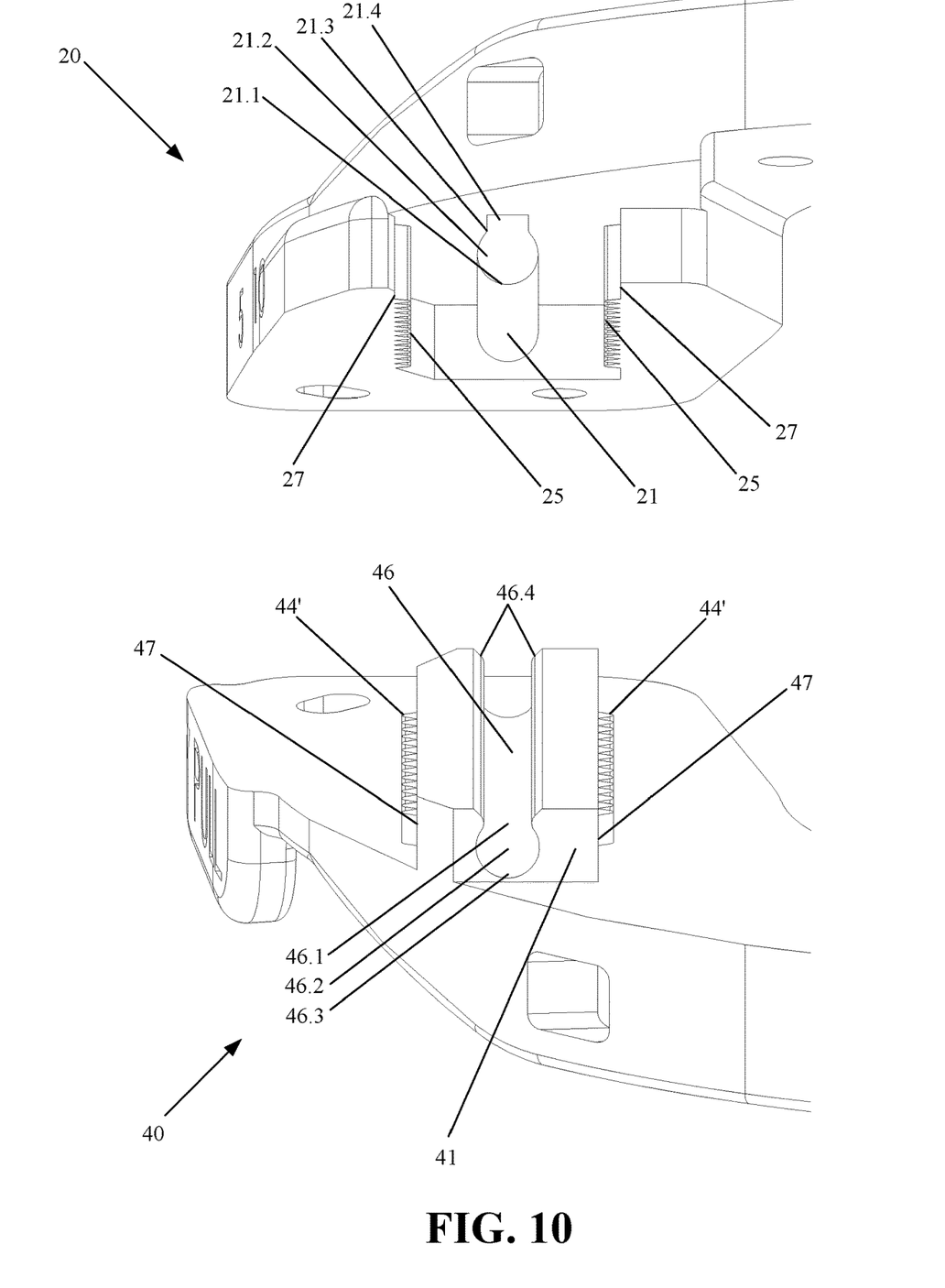
FIG. 10 is a detailed front view of a rib and mating channel of a mandibular advancement device.

FIG. 10 is a detailed front view of a rib and mating channel of a mandibular advancement device. As shown in FIG. 10, a mandibular advancement device includes an upper frame 20 and a lower frame 40. The upper frame can include a rib 21 extending substantially from the front to the back. Walls 27 can be disposed on a left side and a right side of the rib 21 and facing the rib 21. The walls 27 can be parallel to the rib 21. Teeth 25 can be disposed on the parallel walls 27 facing inwards towards the rib 21. The rib 21 can be substantially cylindrical. The rib 21 can have a symmetrical profile. The rib 21 can have a top 21.1, a bottom 21.3, and a middle portion 21.2 disposed between the top 21.1 and the bottom 21.3. The rib 21 can be disposed on a pillar 21.4. The pillar 21.4 can be narrower than the middle portion 21.2 of the rib 21. The middle portion 21.2 of the rib 21 can be wider than the top 21.1 of the rib 21 or the bottom 21.3 of the rib 21.

The lower frame 40 can have a mating portion 41 protruding therefrom. The mating portion 41 can have a channel 46 extending therethrough and sidewalls 47 that are on the left and right sides of the channel 46. The sidewalls 47 of the mating portion 41 can be parallel to the channel 46. The sidewalls 47 of the mating portion 41 can have teeth 44' on the outsides thereof. The teeth 44' can face away from the channel 46.

The channel 46 can have a top 46.1, a bottom 46.3, and a middle portion 46.2 disposed between the top 46.1 and the bottom 46.3. The middle portion 46.2 of the channel 46 can be wider than the top 46.1 of the channel 46 and the bottom 46.3 of the channel 46. The channel can have a beveled opening 46.4. The beveled opening 46.4 can be sized in relative proportions to receive the top 21.1 of the rib 21. When placed together, the rib 21, can slide fore and aft along the beveled opening 46.4 of the channel 46. In the embodiment of FIG. 10, the teeth 44' can be shorter than the height of sidewalls 47 thereby preventing the mating teeth 25 of the upper frame 20 from contacting the teeth 44' prime while the two frames are slidably engaged. Those of skill in the art will appreciate that although the embodiment of FIG. 10 shows shorter teeth 44' on the lower frame 40, shorter teeth alternatively could be substituted in place of teeth 25 and still achieve objects of the invention. The teeth 44' can be shorter than the teeth 25. The width of the beveled opening 46.4 can be narrower than the width of the middle portion 21.2 of the rib 21.

The upper frame 20 and the lower frame 40 can be snapped together such that the rib 21 is pressed into the channel 46. The rib 21 can be wider than the opening 46.4 of the channel 46 such that the channel 46 deforms or deflects slightly in response to a squeezing force to allow the rib to fully enter the channel. When the rib 21 is pressed into the channel 46, the inward facing teeth 25 of the upper frame 20 can engaged the outward facing teeth 44' of the lower frame 40. When engaged, teeth 25 and 44' can restrict the upper frame 20 from sliding with respect to the lower frame 40.

The teeth 25 of the upper frame can opposing in that the teeth 25 are disposed on opposite walls and are facing each other. The rib 21 can be disposed between the opposing teeth 25. The mating portion 41 of the lower frame 46 can include outward facing teeth 44' disposed in relative position and formed in relative proportions to engage the inward facing teeth 25 of the upper frame 20. Although the embodiment of FIG. 10 is shown as having opposing teeth, other embodiments can include just a single set of teeth on only one side of the rib 21. Similarly, although the embodiment of FIG. 10 is shown as having two sets of outwardly facing teeth 44' on the mating portion 41, it is contemplated that other embodiments can include just a single set of outwardly facing teeth on just on side of the mating portion 41.

It will be apparent to those skilled in the art that various modifications and variations can be made in the mandibular advancement device without departing from the spirit or scope of the invention. Thus, it is intended that embodiments of the invention cover the modifications and variations of this invention provided they come within the scope of the appended claims and their equivalents.

What is claimed is:

1. A mandibular advancement device having a first frame and a second frame, the first frame having a first occlusal surface and a first generally U-shaped groove, the second frame having a second occlusal surface and second generally U-shaped groove, the mandibular advancement device comprising:
   a first rib protruding from the first occlusal surface of the first frame;
   a first upstanding sidewall protruding from the first occlusal surface of the first frame;
   a first inner surface of the first upstanding sidewall, the first inner surface generally parallel to, offset from, and facing the first rib;
   a first set of teeth on the first inner surface of the first upstanding wall, the first set of teeth facing the first rib;

a first channel of the second occlusal surface of the second frame, the first channel in relative position to interface with the first rib;

an opening of the first channel on the second occlusal surface, the opening of the first channel having a width that is narrower than a width of the first rib and sized in relative proportions to snappingly retain the first rib;

a second upstanding sidewall protruding from the second occlusal surface of the second frame;

a first outside wall of the second upstanding sidewall, the first outside wall in relative position to interface with the first inner surface of the upstanding first sidewall; and a second set of teeth on the first outside wall of the second upstanding sidewall.

2. The mandibular advancement device of claim 1 further comprising:

a second rib on the first frame; and a second channel on the second frame, the second channel in relative position to interface with the second rib.

3. The mandibular advancement device of claim 1 further comprising:

a beveled portion of the first channel.

4. The mandibular advancement device of claim 1 wherein the first rib is substantially cylindrical.

5. The mandibular advancement device of claim 1 further comprising:

wherein the first set of teeth and the second set of teeth cooperate to secure the first rib with respect to the first channel when the first rib is inserted in the first channel.

6. The mandibular advancement device of claim 5 further comprising:

a third set of teeth facing the first rib;

a fourth set of teeth facing away from the first channel; and wherein the third set of teeth and the fourth set of teeth cooperate to secure first rib with respect to the first channel when the first rib is inserted in the first channel.

7. The mandibular advancement device of claim 5 wherein the second set of teeth is shorter than the second upstanding sidewall.

8. The mandibular advancement device of claim 5 wherein the second set of teeth is shorter than the first set of teeth.

9. A mandibular advancement device having a first frame and a second frame, the first frame having a first occlusal surface and a first generally U-shaped groove, the second frame having a second occlusal surface and second generally U-shaped groove, the mandibular advancement device comprising:

a first rib protruding from the first occlusal surface of the first frame, the first rib having a wider portion disposed between a top of the first rib and a bottom of the first rib;

a first upstanding sidewall protruding from the first occlusal surface of the first frame;

a first inner surface of the first upstanding sidewall, the first inner surface generally parallel to, offset from, and facing the first rib;

a first set of teeth on the first inner surface of the first upstanding wall, the first set of teeth facing the first rib;

a first channel of the second occlusal surface of the second frame, the first channel in relative position to interface with the first rib;

an opening of the first channel on the second occlusal surface, the opening of the first channel having a width that is narrower than a width of the first rib and sized in relative proportions to snappingly retain the first rib;

a second upstanding sidewall protruding from the second occlusal surface of the second frame;

a first outside wall of the second upstanding sidewall, the first outside wall in relative position to interface with the first inner surface of the upstanding first sidewall; a second set of teeth on the first outside wall of the second upstanding sidewall; and wherein the first frame and the second frame are configured to be disposed in a first position and a second position wherein, in the first position, the top of the first rib is slidably disposed on the top of the first channel and wherein, in the second position, the first rib is disposed in the first channel and the first set of teeth are engaged with the second set of teeth, and wherein, upon squeezing the first frame and the second frame together, the first rib of the first frame snaps into the first channel thereby holding the first frame and the second frame together and the first set of teeth and the second set of teeth restrict sliding of the first frame with respect to the second frame.

10. The mandibular advancement device of claim 9 further comprising:

a beveled portion of the first channel.

11. The mandibular advancement device of claim 9 wherein the second set of teeth is shorter than the second upstanding sidewall.

12. The mandibular advancement device of claim 9 further comprising:

a third set of teeth opposite the first set of teeth; and a fourth set of teeth opposite the second set of teeth.

13. The mandibular advancement device of claim 9 further comprising:

a second rib; and a second channel, the second channel having a wider portion disposed between a top of the second channel and a bottom of the second channel, the second channel disposed in relative position to interface with the second rib and in relative proportions to receive a portion of the second rib therein.

14. A mandibular advancement device having a first frame and a second frame, the first frame having a first occlusal surface and a first generally U-shaped groove, the second frame having a second occlusal surface and second generally U-shaped groove, the mandibular advancement device comprising:

a first set of upstanding sidewalls on the first occlusal surface of the first frame;

a first rib disposed between the first set of upstanding sidewalls;

a first set of teeth on the first set of upstanding sidewalls, the first set of teeth facing the first rib;

a second set of upstanding sidewalls on the first occlusal surface of the first frame;

a second rib disposed between the second set of upstanding sidewalls;

a second set of teeth on the second set of upstanding sidewalls, the second set of teeth facing the second rib;

a third set of teeth on the second occlusal surface disposed in relative position to interface with the first set of teeth;

a first channel disposed between the third set of teeth, the first channel dimensioned in relative proportions and disposed in relative position to receive the first rib;

a fourth set of teeth on the second occlusal surface disposed in relative position to interface with the second set of teeth; and a second channel disposed between the fourth set of teeth, the second channel dimensioned in relative proportions and disposed in relative position to receive the second rib.

15. The mandibular advancement device of claim 14 further comprising:
a middle portion of the first rib, the middle portion of the first rib wider than a top of the first rib and a bottom of the first rib; and
a middle portion of the second rib, the middle portion of the second rib wider than a top of the second rib and a bottom of the second rib.

16. The mandibular advancement device of claim 14 wherein the first frame and the second frame are configured to be disposed in a first position and a second position;
wherein, in the first position, the first and second ribs are slidably disposed on the first and second channels, respectively; and
wherein, in the second position, the first and second ribs are disposed in the first and second channels, respectively, and the first and second sets of horizontally opposed teeth are engaged with the third and fourth sets of teeth.

17. The mandibular advancement device of claim 16 wherein the first and second frames are configured to releasably snap together from the first position into the second position thereby securing the first frame with respect to the second tray.

18. The mandibular advancement device of claim 14 further comprising: a beveled portion of the first channel.

19. The mandibular advancement device of claim 14 wherein the third set of teeth is shorter than a sidewall of the first channel.

* * * * *